United States Patent [19]
Philippossian et al.

[11] Patent Number: 5,053,433
[45] Date of Patent: Oct. 1, 1991

[54] COSMETIC COMPOSITION WITH ANTICELLULITIC AND SLIMMING ACTION, IN WHICH THE ACTIVE PRINCIPLE IS A 1-HYDROXYALKYLXANTHINE

[75] Inventors: Georges Philippossian, Lausanne, Switzerland; Jean-Pierre Laugier, Antony; Liliane Ayache, Paris, both of France

[73] Assignee: Société Anonyme Dite: L'Oreal, Paris, France

[21] Appl. No.: 538,694

[22] Filed: Jun. 18, 1990

Related U.S. Application Data

[63] Continuation of Ser. No. 213,011, Jun. 29, 1988, abandoned.

[30] Foreign Application Priority Data

Jun. 30, 1987 [LU] Luxembourg ............................ 86934

[51] Int. Cl.⁵ .......................... A61K 7/48; A61K 9/10; A61K 9/12; A61H 23/02
[52] U.S. Cl. ...................................... 514/909; 128/55; 424/47; 514/937; 514/938; 514/944
[58] Field of Search .......................................... 514/909

[56] References Cited

U.S. PATENT DOCUMENTS 4,288,433  9/1981  Koulbanis .......................... 514/909

FOREIGN PATENT DOCUMENTS 7733374  6/1978  France .
8020333  3/1982  France .
86/00401  1/1987  Int'l Pat. Institute .............. 514/256

OTHER PUBLICATIONS

Beavo et al., Molecular Pharmacology, 1971, vol. 74, No. 7.
Chem. Abs., 1973, vol. 78, 238342, Hinze.
Chem. Abs., 1987, vol. 106, 213648m, Abstract of Germ. Offen. DE. 3,525,801 (1/87 Gebert).
"Effects of Xanthine Derivatives on Lipolysis and on Adenosine 3',5'-Monophosphate Phosphodiesterase Activity", Chemical Abstracts, vol. 74, No. 7, Feb. 1971, Resume No. 40820b.
Molecular Pharmacology, vol. 6, No. 6, "Effects of Xanthine Derivatives on Lipolysis and on Adenosine 3',5'-Monophosphate Phosphodiesterase Activity", Beavo et al., Nov. 1970, pp. 597-603.

Primary Examiner—Dale R. Ore
Attorney, Agent, or Firm—Wegner, Cantor, Mueller & Player

[57] ABSTRACT

Cosmetic composition.

This composition contains, as active compound in a suitable cosmetic carrier, at least one 1-hydroxyalkylxanthine of formula:

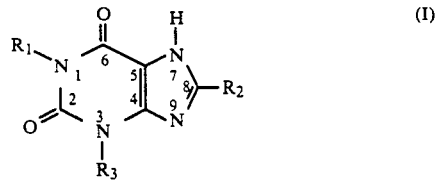

Use for its slimming and anticellulitic action.

13 Claims, No Drawings

COSMETIC COMPOSITION WITH ANTICELLULITIC AND SLIMMING ACTION, IN WHICH THE ACTIVE PRINCIPLE IS A 1-HYDROXYALKYLXANTHINE

This application is a continuation of U.S. application Ser. No. 07/213,011 filed June 29, 1988, now abandoned.

The present invention relates to a cosmetic composition for the skin, particularly a composition with slimming and anticellulitic action.

Cellulitis is the result of an inflammation which is seen as a more or less considerable increase in the volume of the adipocytes situated in the deep part of the skin.

This increase is due to an excess of fats inside these cells, which are stored in the form of triglycerides. Overall hypertrophy of the fat cells causes an increase in the thickness of the skin in the cellulitic regions.

A phenomenon known by the name of "orange peel" is also seen, and corresponds to a stretching of the membrane walls in the hypodermis.

Lastly, the suppleness of the cellulitic skin is modified because of a considerable hydrous retention in the skin region.

Within the adipose cell there exists an enzymatic degradation system which acts on the storage triglycerides.

The enzyme directly responsible for this degradation, and hence for lipolysis, is present in the adipocyte in an inactive state, and is the triglyceride lipase. To become active, this enzyme must be subjected to the action of cyclic AMP. The intensity of the degradation of the fats, and thus of slimming, depends on the quantity of the latter. The content of cyclic AMP is the result of an equilibrium between its synthesis and its degradation.

The enzyme responsible for the synthesis of cyclic AMP is adenylcyclase, and that responsible for its degradation is phosphodiesterase.

It follows from this that to increase the quantity of cyclic AMP it is necessary, therefore, to affect either adenylcyclase or phosphodiesterase.

In effect, phosphodiesterase destroys cyclic AMP by converting it into 5'AMP, so that it cannot act as the lipolysis activator.

It is essential, therefore, to inhibit the action of phosphodiesterase so as to have a high content of cyclic AMP in the adipocyte region in order to stimulate lipolytic activity.

More precisely, inhibition of phosphodiesterase prevents or at least limits the rate of degradation of cyclic AMP, which can therefore activate the triglyceride lipase.

The latter will convert the triglycerides into free fatty acids and glycerol. The fatty acids will thus be released into the bloodstream and employed in the organism as a source of energy.

Among the various inhibitors of phosphodiesterase which have been recommended, particular mention may be made of xanthic bases and more particularly theophylline, caffeine and theobromine.

It has now just been found that it was possible to obtain a good inhibition of phosphodiesterase by employing new xanthine derivatives, especially 1-hydroxyalkylxanthines.

The studies which have been carried out have made it possible to demonstrate, in fact, that 1-hydroxyalkylxanthines had a phosphodiesterase-inhibiting action which was markedly superior to that of the xanthic bases employed hitherto.

The subject of the present invention, as a new industrial product, is therefore a cosmetic composition with slimming and anticellulitic action, containing, in a suitable cosmetic carrier, as active compound, at least one 1-hydroxyalkylxanthine corresponding to the following general formula:

$$\text{(I)}$$

[Structure of xanthine with substituents $R_1$ on $N_1$, $R_3$ on $N_3$, and $R_2$ on $C_8$]

in which:
- $R_1$ denotes a $C_2$–$C_5$ ω-hydroxy-n-alkyl or $C_3$–$C_5$ (ω−1)-hydroxy-n-alkyl group,
- $R_2$ denotes a hydrogen atom or a methyl or ethyl radical, and
- $R_3$ denotes a $C_1$–$C_4$ alkyl group, the number of carbon atoms in $R_1+R_3$ being between 4 and 9, and the salts of the said compounds of formula (I).

According to a preferred embodiment, the active compound in the compositions according to the invention is a compound of formula (I) in which $R_3$ denotes a propyl radical.

Among the active compounds of formula (I), the following may be mentioned in particular:
1) 1-(2-hydroxyethyl)-3-propylxanthine,
2) 1-(2-hydroxyethyl)-3-isobutylxanthine,
3) 1-(2-hydroxyethyl)-3-isobutyl-8-methylxanthine,
4) 1-(2-hydroxypropyl)-3-propylxanthine,
5) 1-(2-hydroxypropyl)-3 propyl-8-methylxanthine,
6) 1-(2-hydroxypropyl)-3-butylxanthine,
7) 1-(3-hydroxypropyl)-3-propylxanthine,
8) 1-(3-hydroxypropyl)-3-propyl-8-methylxanthine,
9) 1-(3-hydroxypropyl)-3-propyl-8-ethylxanthine,
10) 1-(3-hydroxypropyl)-3-butylxanthine,
11) 1-(3-hydroxypropyl)-3-isobutylxanthine,
12) 1-(3-hydroxypropyl)-3-isobutyl-8-methylxanthine,
13) 1-(3-hydroxybutyl)-3-methylxanthine,
14) 1-(3-hydroxybutyl)-3-ethylxanthine,
15) 1-(3-hydroxybutyl)-3-ethyl-8-methylxanthine,
16) 1-(3-hydroxybutyl)-3-propylxanthine,
17) 1-(3-hydroxybutyl)-3-isobutylxanthine,
18) 1-(4-hydroxybutyl)-3-ethylxanthine,
19) 1-(4-hydroxybutyl)-3-propylxanthine,
20) 1-(4-hydroxybutyl)-3-propyl-8-methylxanthine,
21) 1-(4-hydroxybutyl)-3-butylxanthine,
22) 1-(4-hydroxybutyl)-3-isobutyl-8-methylxanthine,
23) 1-(4-hydroxypentyl)-3-methylxanthine,
24) 1-(4-hydroxypentyl)-3-propylxanthine,
25) 1-(5-hydroxypentyl)-3-methylxanthine,
26) 1-(5-hydroxypentyl)-3-propylxanthine and
27) 1-(5-hydroxypentyl)-3-propyl-8-methylxanthine.

Among the salts of the compounds of formula (I), there may be mentioned in particular the salts of alkali metals such as sodium and potassium, ammonium salts and organic amine salts such as ethanolamine, diethanolamine or isopropanolamine salts.

The cosmetic compositions according to the invention contain from 0.01 to 5% and preferably from 0.1 to 1% by weight of at least one 1-hydroxyalkylxanthine of formula (I), based on the total weight of the composition.

The compositions according to the invention may be presented in various forms, particularly in the form of lotions, emulsion, anhydrous or hydroalcoholic gels, emulsified gels or in the form of aerosol foams.

When the compositions are in the form of lotions, that is to say more particularly of aqueous solutions, they contain a solubilizing agent for the active compound such as, for example, sodium benzoate or else triethanolamine salicylate in a proportion of between 0.5 and 30% by weight.

When the compositions according to the invention are in the form of emulsions, then in addition to the active compound they contain:

from 0.5 to 30% of a solubilizing agent such as mentioned above,
from 3 to 50% of at least one vegetable, mineral or synthetic oil,
from 1 to 10% of a fatty alcohol,
from 0.5 to 8% of a $C_8$–$C_{18}$ fatty acid, and
from 0.5 to 12% of an anionic, nonionic or cationic emulsifying agent, the remainder consisting of water.

Among the vegetable or animal oils, there may be mentioned, for example, sweet almond oil, avocado oil, castor oil, olive oil, jojoba oil, perhydrosqualene, calophyllum oil, lanolin and its derivatives, sunflower oil, wheatgerm oil, sesame oil, groundnut oil, grapeseed oil, corn oil, nut oil, karite butter, Shorea robusta fat, palm oil, and the like.

Among the mineral oils, there may be mentioned, for example, liquid paraffin and, among the synthetic oils, ethyl and isopropyl palmitates, alkyl myristates such as isopropyl, butyl and cetyl myristate, hexyl stearate, triglycerides of octanoic and decanoic acids (for example the product sold by Dynamit Nobel under the name of "Miglyol"), cetyl ricinoleate, stearyl octanoate (purcellin oil) and hydroxylated polyisobutene.

Among the fatty alcohols, there may be mentioned cetyl alcohol, stearyl alcohol, myristyl alcohol, hydroxystearyl alcohol, oleyl alcohol and isostearyl alcohol.

Among the fatty acids, there may be mentioned stearic acid, myristic acid, palmitic acid, oleic acid and linoleic acid.

Among the emulsifying agents of the anionic, nonionic or cationic type, those particularly preferred are: glycerol mono- and diesters, polyoxyethylenated or otherwise, sorbitan esters, polyoxyethylenated or otherwise, marketed by ICI under the names of "Tween" and "Span", polyoxyethylenated fatty alcohols sold by ICI under the name of "Brig" and polyoxyethylenated fatty acids sold by ICI under the name of "Mirj".

When the compositions are in the form of clear gels, they may be either anhydrous or hydroalcoholic.

When the gels are in anhydrous form, they contain:
from 5 to 90% of an alcohol such as ethanol, and
from 0.2 to 5% of a gelling agent.

Among the gelling agents, particular mention may be made of cellulose derivatives such as hydroxyethyl cellulose.

When the gels are in hydroalcoholic form, they contain:
from 5 to 70% of an alcohol such as ethanol, and
from 0.2 to 3% of a carboxyvinyl polymer such as those sold under the names of "Carbopol 934, 940 and/or 941", neutralized beforehand, the remainder consisting of water.

The compositions according to the invention may also contain other ingredients which are conventional in compositions of these various types, such as, for example, perfumes, colorants, stabilizers or emollients, and the like.

Another subject of the present invention is a process for treating the skin with a view to a slimming action, this process consisting in applying to the parts of the body to be treated, by massage, a sufficient quantity of a composition according to the invention.

This massage treatment process is more particularly employed when the compositions are in the form of emulsions, of creams, of gels or of aerosol foams.

As a general rule, the duration of the treatment is variable, but the latter gives quite satisfactory results when it is carried out for a period of 2 to 8 weeks, at a rate of one application daily.

Another subject of the present invention is a particular process for the treatment of cellulitis with the aid of the compositions according to the invention which are in the form of lotions, this process consisting in applying the technique known as transcutaneous electrophoresis to the subject to be treated.

On this subject, it will be recalled that this treatment technique consists in making an ionizable substance migrate through the skin and the surface tissues of the skin by means of a low-intensity direct current, to obtain an impregnation of the subdermic conjunctive region to be treated.

Devices of various types can be employed to perform this treatment, especially the apparatus known by the name of "Presti-6" marketed by France Matériel.

According to this process, the electrodes are covered with a layer of cotton wool, and the treating electrode, saturated with the composition according to the invention, is applied to the part of the body to be treated, the opposite electrode being applied to another part of the body.

If the product to be ionized is electronegative, the treating electrode carrying the product according to the invention is connected to the negative pole of the apparatus.

According to a particular embodiment, it is possible to saturate both electrodes with the product according to the invention and to reverse the electrode connections during the treatment.

As a general rule, the ionization period is of the order of 10 minutes. The current intensity may vary from 4 to 6 milliamperes, depending on the cutaneous reaction of the subjects to be treated.

This treatment is preferably carried out at a rate of 3 ionizations weekly, this being done for a period of 4 to 8 weeks.

The active compounds employed in the compositions according to the invention may be prepared according to one of the methods described below:

Method A)

A uracil of formula:

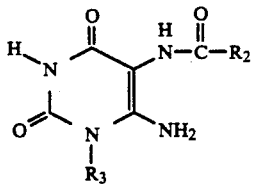

is reacted with an alkylating agent of formula $R_1-X$, where $R_1$, $R_2$ and $R_3$ are such as defined in the general formula (I), except that $R_1$ is other than ω-hydroxybutyl and where X is a halogen, preferably bromine, in a mutual solvent for the reactants, such as, for example, dimethylformamide (DMF), dimethyl sulphoxide (DMSO) or hexamethylphosphorotriamide (HMPT), at a temperature of between 20° and 40° C., and in the presence of an alkali metal hydroxide, for example sodium hydroxide in solid form. The reaction is preferably carried out in DMF at 20° C.

The ring closure of the alkylation product obtained, of formula (III), is then performed in a solution of an alkali metal hydroxide between 20° and 100° C., according to the reaction scheme below:

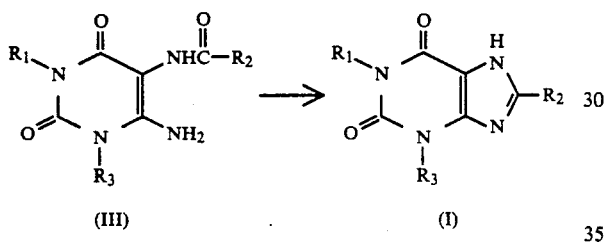

Although the derivative of general formula (III) can be isolated, it is preferred to perform this ring closure directly without isolating or purifying this derivative. To this end, the reaction medium is neutralized and the solvent is evaporated off, and then the residue is dissolved in a solution of alkali metal hydroxide and is heated under reflux.

Method B)

According to a variant, an alkylation of the uracil (II) is carried out with an agent containing a functional group capable of being converted into a hydroxyl group, for example a $-COO-R_4$ group, according to the following reaction scheme:

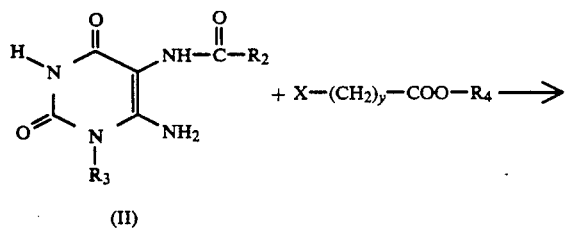

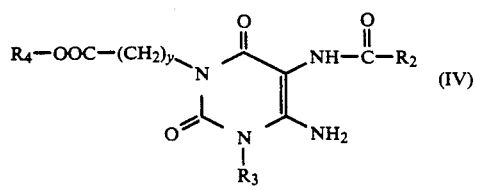

in which
$R_2$, $R_3$ and X are as defined above,
y is between 1 and 4, and
$R_4$ is an alkyl group.

This alkylation reaction is carried out as in the case of A) in a mutual solvent for the reactants, such as DMF, DMSO or HMPT, at a temperature of between 20° and 40° C., and in the presence of an alkali metal hydroxide in solid form. A ring closure and an accompanying hydrolysis of the ester (IV) are then performed in an alkali metal hydroxide between 20° and 100° C., according to the following reaction scheme:

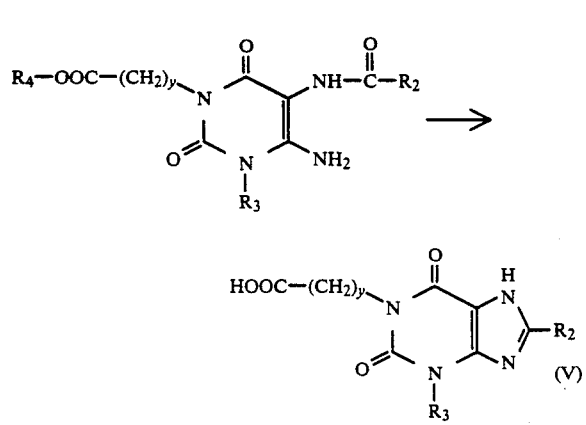

Although the acid (V) can be reduced directly to alcohol, it is preferred to reesterify the acid (V) with an alcohol such as methanol, ethanol or propanol, under reflux, to obtain the corresponding ester which is reduced in a known manner, for example in the presence of LiAlH₄ in THF, to obtain the following product:

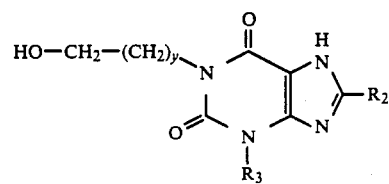

It can be seen, therefore, that according to this second method, ω-hydroxyalkylxanthines are always obtained.

Method C)

According to this last method, (ω-1)-hydroxyalkylxanthines are prepared by alkylating the uracil of general formula (II) above with an alkylating agent of formula $CH_2=CH-(CH_2)_p-X$, where $R_2$, $R_3$ and X are as defined above and p is 1, 2 or 3. The alkylation is carried out in the same conditions as according to methods A) and B), namely in a mutual solvent for the reactants, such as DMF, DMSO or HMPT, at a temperature of between 20° and 40° C., and in the presence of an alkali metal hydroxide in solid form. A ring closure is then performed in a solution of an alkali metal hydroxide between 20° and 100° C., according to the following reaction scheme:

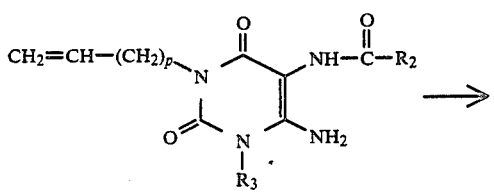

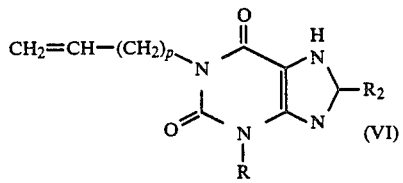

It finally remains to hydrate the double bond according to a Markovnikoff type addition, to obtain the following product

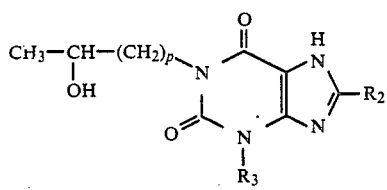

This addition may be carried out according to two variants:

Variant A: by means of dilute sulphuric acid at a temperature of approximately 100° C. for several days;

Variant B: by the oxymercuration-reductive demercuration method in the presence of mercury acetate and then of NaBH₄ (R. C. Larock, Solvomercuration/-Demercuration Reactions in Organic Synthesis, Springer, Berlin, 1986, Chap. 2).

A number of examples of preparation of the active compounds of formula (I), as well as examples of anticellulitic compositions according to the invention will now be given by way of illustration and without any limitation being implied.

EXAMPLE 1

1-(5-Hydroxypentyl)-3-propyl-8-methylxanthine (Method A, compound No. 27)

22.6 g (0.1 mole) of 1-propyl-5-acetylamino-6-aminouracil (II) ($R_3$=propyl, $R_2$=methyl) are suspended under nitrogen in 200 ml of anhydrous dimethylformamide (DMF). 21.7 g (0.13 mole) of 5-bromo-1-pentanol are added, and 6 g (0.15 mole) of powdered solid NaOH are then added, with stirring, in 1 g portions at a time at hourly intervals. After the third addition, the suspension has dissolved completely. The mixture is left to stand overnight to complete the reaction. The solvent is evaporated off in the rotary evaporator at 13 Pa and at 40° C. The oily residue, which is the uracil (III) ($R_1$=5-hydroxypentyl, $R_3$=propyl, $R_2$=methyl), which is not purified, is dissolved in 100 ml of 10% NaOH and the solution is refluxed for 2 hours. The solution is cooled in an ice bath and is neutralized with acetic acid to pH 5. The precipitated product is filtered off, is washed with cold water and is dried in a vacuum oven. It is dissolved in 500 ml of ethanol and the solution is decolorized with active charcoal overnight. The product is precipitated by adding 1 liter of water, and is filtered off, and the active charcoal treatment is repeated. The dried product is recrystallized twice from 120 ml of dioxane.

Yield: 23.5 g (80%); colourless crystals; melting point: 184°-185° C.

EXAMPLE 2

1-(4-Hydroxybutyl)-3-butylxanthine (Method B, compound No. 21)

11.3 g (0.05 mole) of 1-butyl-5-formylamino-6-aminouracil (II) ($R_3$=butyl, $R_2$=H) are dissolved under nitrogen in 200 ml of DMF. 10.6 ml (0.075 mole) of ethyl 4-bromobutyrate are added, followed, with good stirring, by 2 g of (0.05 mole) of powdered solid NaOH in hourly 0.5 g portions. When the addition has been completed, the mixture is left to react overnight again. The solvent is evaporated off and the oily residue of (IV) (substituent in the 1 position=—$(CH_2)_3$COOEt) is dissolved in 100 ml of 10% NaOH. This solution is refluxed for ½ hour. It is cooled, neutralized with acetic acid to pH 5, and the precipitate formed is filtered off and dried.

Yield: 9.2 g (60%) of crude xanthine (V) (substituent in the 1 position=—$(CH_2)_3$COOH, $R_3$=butyl, $R_2$=H).

Without being purified, the product is esterified with 200 ml of methanol containing 1 ml of concentrated sulphuric acid under reflux for 5 hours. The solution is concentrated down to a small volume and 50 ml of water are added. The ester precipitate which is formed (substituent in the 1 position=—$(CH_2)_3$COOMe) is filtered off, washed and dried.

Yield: 9 g (93%).

The product is dissolved in 200 ml of anhydrous tetrahydrofuran (THF), without being purified, and is cooled to between 0° and −10° C., and a solution containing 2.13 g (0.056 mole) of LiAlH₄ in 150 ml of anhydrous THF is added dropwise. When the addition has been completed, the mixture is left to react for another 2 hours at 0° C., and then excess LiAlH₄ is destroyed by adding 50 ml of water. The mixture is acidified with concentrated hydrochloric acid to pH 2 and the THF is then evaporated off. The residual aqueous solution is extracted continuously with dichloromethane overnight. The organic extract is dried and the solvent is evaporated off. The slightly coloured solid residue (6.1 g) is recrystallized twice from acetone.

Yield: 4.6 g (33% based on II); colourless crystals; melting point: 122°-123° C.

EXAMPLE 3

1-(3-Hydroxybutyl)-3-isobutylxanthine (Method C/variant A, compound No. 17)

11.3 g (0.05 mole) of 1-isobutyl-5-formylamino-6-aminouracil (II) ($R_3$=isobutyl, $R_2$=H) are dissolved in 200 ml of DMF. 8.8 g (0.065 mole) of 4-bromo-1-butene are added, followed by 3 g (0.075 mole) of powdered NaOH in hourly 0.5 g portions, with stirring. The mixture is left overnight and the solvent is then evaporated off under vacuum. The crude residue is taken up in 100 ml of 10% NaOH and is refluxed for ½ hour. The solution is cooled, is neutralized with acetic acid to pH 5, the precipitate formed is filtered off and is dried. 8.5 g of crude solid product (VI) ($R_5$=3-butenyl, $R_3$=isobutyl, $R_2$=H) are obtained. This product is purified by a pass through a silica column (85 g), chloroform being used as eluent; 6.5 g of colourless product are obtained.

A mixture containing 6 g of the above compound in 100 ml of 20% sulphuric acid is heated to 100° C. for 4 days. It is cooled and neutralized with 50% potassium hydroxide to pH 5. The solution is evaporated down to dryness, the residue is taken up in 100 ml of boiling absolute ethanol and the insoluble material is filtered off. The filtrate is freed from the solvent; a coloured residue (6.4 g) is obtained and is passed through a silica column (650 g), a chloroform/methanol gradient (0–5% methanol) being used as eluent. The expected xanthine is recrystallized twice from acetone.

Yield: 4.5 g (33% based on II); melting point: 141°–142° C.

EXAMPLE 4

1-(2-Hydroxypropyl)-3-butylxanthine (Method C/variant B, compound No. 6)

16 g (0.050 mole) of mercury acetate are dissolved in 250 ml of water. 12.4 g (0.05 mole) of 1-allyl-3-butylxanthine (prepared as above from 1-butyl-5-formylamino-6-aminouracil and allyl bromide) dissolved in 250 ml of THF are added dropwise with stirring over 10 minutes. A precipitate forms after a few minutes. Stirring is continued for 30 minutes and the mixture is then cooled in an ice bath. 68 ml of 3N NaOH are added, followed, dropwise, by 60 ml of a freshly prepared 0.5M solution of NaBH$_4$ in 3N NaOH. When the addition has been completed, stirring is continued for another 15 minutes. The solution is neutralized with 6N HCl to pH 4–5 (approximately 60 ml). The solution is saturated with NaCl and the xanthine is extracted with dichloromethane (3×200 ml). The organic extract is dried and the solvent is evaporated off; 12.9 g of crude product containing 20% of starting material are obtained. The products are separated by passing the mixture through a silica column and eluting the starting material with chloroform, and then the hydroxylated xanthine (9.5 g) with chloroform/methanol (95/5). 2 recrystallizations from water are carried out, to give 8.5 g (64%) of pure product; melting point: 157°–158° C.

The methods of preparation of the remaining compounds and their melting points are given in Table I below.

TABLE I

| Compound No. | Method of preparation | MP (°C.) | Recrystallization solvent |
| --- | --- | --- | --- |
| 1 | A | 178–179 | Acetone |
| 2 | A | 200–202 | Acetone |
| 3 | A | 227–229 | Chloroforme |
| 4 | C/variant B | 150–152 | Chloroforme |
| 5 | C/variant A | 196–197 | Methanol |
| 7 | A | 145–146 | Methanol |
| 8 | A | 221–222 | Methanol |
| 9 | A | 196–198 | Water |
| 10 | A | 111–112 | Water |
| 11 | A | 159–160 | Acetone |
| 12 | A | 248–250 | Ethanol |
| 13 | C/variant A | 200–201 | Acetone |
| 14 | C/variant A | 217–218 | Water |
| 15 | C/variant A | 212–213 | Water |
| 16 | C/variant A | 163–164 | Acetone |
| 18 | B | 207–208 | Water |
| 19 | B | 173–174 | Acetone |
| 20 | B | 192–193 | Water |
| 22 | B | 211–212 | Methanol |
| 23 | C/variant A | 180–181 | Acetone |
| 24 | C/variant B | 153–154 | Acetone |
| 25 | A | 190–191 | Water |
| 26 | A | 151–152 | Water |

EXAMPLES OF COMPOSITIONS

Example A

Slimming Liquid to be Ionized

| | |
| --- | --- |
| 1-(5-Hydroxypentyl)-3-propyl-8-methylxanthine | 0.2 g |
| Sodium benzoate | 3.0 g |
| Stabilizers | 0.2 g |
| Water q.s. | 100 g |

On applying 4 times weekly for 3 or 4 weeks, an excellent result is found with regard to the decrease in cellulitis of the thighs, the hips and the knees.

Example B

Slimming Oil-in-Water Emulsion

| | |
| --- | --- |
| 1-(5-Hydroxypentyl)-3-propyl-8-methylxanthine | 0.5 g |
| Sodium benzoate | 3.0 g |
| Polyethylene glycol 400 | 3.0 g |
| Propylene glycol | 4.0 g |
| Triethanolamine | 0.6 g |
| Sweet almond oil | 2.0 g |
| Isopropyl myristate | 1.0 g |
| Esters of capric/caprylic acids and of $C_{12}$–$C_{18}$ fatty alcohols, sold by Henkel under the name "Cetiol LC-DEO" | 1.0 g |
| Cetyl alcohol | 3.0 g |
| Stearic acid | 3.0 g |
| Non-autoemulsifiable glycerol mono- and distearate | 3.0 g |
| Perfumes | 0.1 g |
| Stabilizers | 0.2 g |
| Water q.s. | 100 g |

This emulsion, applied regularly every day to the hips and to the thighs makes it possible to obtain a decrease in cellulitis and in fatty rolls after 4 to 6 weeks' treatment.

Example C

Slimming Hydroalcoholic Gel

| | |
| --- | --- |
| Carbopol 941 | 1.0 g |
| Triethanolamine | 1.0 g |
| 1-(3-Hydroxybutyl)-3-ethylxanthine | 0.4 g |
| 95% Ethanol | 60.0 g |
| Glycerol | 3.0 g |
| Propylene glycol | 2.0 g |
| Water q.s. | 100 g |

A decrease in cellulitis is observed on the thighs and on the hips following daily application for 3 to 4 weeks.

Example D

Slimming Anhydrous Gel

| | |
| --- | --- |
| 1-(2-Hydroxyethyl)-3-isobutyl-8-methylxanthine | 1.0 g |
| Absolute ethanol | 61.2 g |
| Hydroxyethyl cellulose | 0.8 g |
| Propylene glycol | 25.0 g |
| Polyethylene glycol | 12.0 g |

This gel, applied 4 times weekly for approximately 4 weeks, results in a decrease in cellulitis and in fatty rolls on the hips and the thighs.

We claim:

1. A cosmetic composition with slimming and anticellulitic action comprising, in a cosmetic carrier, as active compound, at least one 1-hydroxyalkylxanthine corresponding to the following formula:

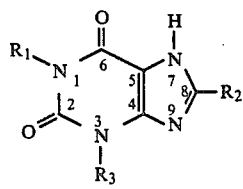

in which:
- $R_1$ denotes a $C_2$-$C_5$ ω-hydroxy-n-alkyl or $C_3$-$C_5$ (ω−1)-hydroxy-n-alkyl group,
- $R_2$ denotes a hydrogen atom or a methyl or ethyl radical, and
- $R_3$ denotes a $C_1$-$C_4$ alkyl group, the number of carbon atoms in $R_1 + R_3$ being between 4 and 9, or a salt of said compound in an effective amount.

2. The composition according to claim 1, wherein the active compound is a compound of formula (I) in which $R_3$ denotes a propyl radical.

3. The composition according to claim 1, wherein the active compound is selected from the group consisting of:
1) 1-(2-hydroxyethyl)-3-propylxanthine,
2) 1-(2-hydroxyethyl)-3-isobutylxanthine,
3) 1-(2-hydroxyethyl)-3-isobutyl-8-methylxanthine,
4) 1-(2-hydroxypropyl)-3-propylxanthine,
5) 1-(2-hydroxypropyl)-3-propyl-8-methylxanthine,
6) 1-(2-hydroxypropyl)-3-butylxanthine,
7) 1-(3-hydroxypropyl)-3-propylxanthine,
8) 1-(3-hydroxypropyl)-3-propyl-8-methylxanthine,
9) 1-(3-hydroxypropyl)-3-propyl-8-ethylxanthine,
10) 1-(3-hydroxypropyl)-3-butylxanthine,
11) 1-(3-hydroxypropyl)-3-isobutylxanthine,
12) 1-(3-hydroxypropyl)-3-isobutyl-8-methylxanthine,
13) 1-(3-hydroxybutyl)-3-methylxanthine,
14) 1-(3-hydroxybutyl)-3-ethylxanthine,
15) 1-(3-hydroxybutyl)-3-ethyl-8-methylxanthine,
16) 1-(3-hydroxybutyl)-3-propylxanthine,
17) 1-(3-hydroxybutyl)-3-isobutylxanthine,
18) 1-(4-hydroxybutyl)-3-ethylxanthine,
19) 1-(4-hydroxybutyl)-3-propylxanthine,
20) 1-(4-hydroxybutyl)-3-propyl-8-methylxanthine,
21) 1-(4-hydroxybutyl)-3-butylxanthine,
22) 1-(4-hydroxybutyl)-3-isobutyl-8-methylxanthine,
23) 1-(4-hydroxypentyl)-3-methylxanthine,
24) 1-(4-hydroxypentyl)-3-propylxanthine,
25) 1-(5-hydroxypentyl)-3-methylxanthine,
26) 1-(5-hydroxypentyl)-3-propylxanthine, and
27) 1-(5-hydroxypentyl)-3-propyl-8-methylxanthine.

4. The composition according to claim 1 comprising from 0.01 to 5% by weight of at least one active compound of formula (I), based on the total weight of the composition.

5. The composition according to claim 1 in the form of an aqueous solution containing a solubilizing agent for the active compound in a proportion of between 0.5 and 30% by weight.

6. The composition according to claim 1 in the form of an emulsion containing:
- from 0.5 to 30% of a solubilizing agent,
- from 3 to 50% of at least one vegetable, mineral or synthetic oil,
- from 1 to 10% of a fatty alcohol,
- from 0.5 to 8% of a $C_8$-$C_{18}$ fatty acid and,
- from 0.5 to 12% of an anionic, nonionic or cationic emulsifying agent, the remainder consisting of water.

7. The composition according to claim 5, wherein the solubilizing agent is sodium benzoate or triethanolamine salicylate.

8. The composition according to claim 1 in anhydrous form, containing:
- from 5 to 90% of an alcohol, and
- from 0.2 to 5% of a gelling agent.

9. The composition according to claim 1 in the form of a hydroalcoholic gel containing:
- from 5 to 70% of an alcohol, and
- from 0.2 to 3% of a neutralized polymer, the remainder consisting of water.

10. The composition according to claim 1, further comprising cosmetic ingredients wherein the ingredients are perfumes, colorants, stabilizers or emollients.

11. The composition according to claim 1 comprising 0.1 to 1% by weight of at least one active compound of formula (I), based on the total weight of the composition.

12. The composition according to claim 8, wherein the alcohol is ethanol.

13. The composition according to claim 9, wherein the alcohol is ethanol.

* * * * *